United States Patent [19]
Easley et al.

[11] Patent Number: 5,441,496
[45] Date of Patent: Aug. 15, 1995

[54] LASER DELIVERY SYSTEM WITH SOFT TIP

[75] Inventors: James C. Easley, St. Charles, Mo.; Stanley Chang, Scarsdale, N.Y.

[73] Assignee: Infinitech, Inc., St. Louis, Mo.

[21] Appl. No.: 48,149

[22] Filed: Apr. 15, 1993

[51] Int. Cl.$^6$ .......................... A61B 17/36; A61F 9/00
[52] U.S. Cl. .......................... 606/15; 606/4; 606/16; 604/902
[58] Field of Search .............. 606/4, 5, 6, 14, 15, 606/16; 604/22, 902, 7

[56] References Cited

U.S. PATENT DOCUMENTS

| | | | |
|---|---|---|---|
| 3,865,666 | 2/1975 | Shoney | 604/103 |
| 4,299,227 | 11/1981 | Lincoff | 606/192 |
| 4,316,465 | 2/1982 | Dotson, Jr. | 604/22 |
| 4,537,193 | 8/1985 | Tanner | 606/4 |
| 4,583,539 | 4/1986 | Karlin et al. | 606/4 |
| 4,607,622 | 8/1986 | Fritch et al. | 606/4 |
| 4,702,733 | 10/1987 | Wright et al. | 604/34 |
| 4,857,047 | 8/1989 | Amoils | 604/30 |
| 5,120,323 | 6/1992 | Shockey et al. | 606/194 |
| 5,123,902 | 6/1992 | Muller et al. | 606/5 |
| 5,192,290 | 3/1993 | Hilal | 606/159 |

FOREIGN PATENT DOCUMENTS 9218075  10/1992  WIPO ......................... 606/4

*Primary Examiner*—Stephen C. Pellegrino
*Assistant Examiner*—Sonya C. Harris
*Attorney, Agent, or Firm*—Polster, Lieder, Woodruff & Lucchesi

[57] ABSTRACT

A laser delivery system for ophthalmic surgery and the like includes a handpiece terminating distally in a probe, a laser connector, and an optical fiber for transmitting laser light from a laser source to an eye to be treated. The optical fiber extends substantially through the handpiece probe. The probe also includes a fluid path from the distal end thereof to the interior of the handpiece body. The probe has a soft tip to reduce the possibility of injury to the interior of the eye by contact with the metal portion of the probe.

6 Claims, 2 Drawing Sheets

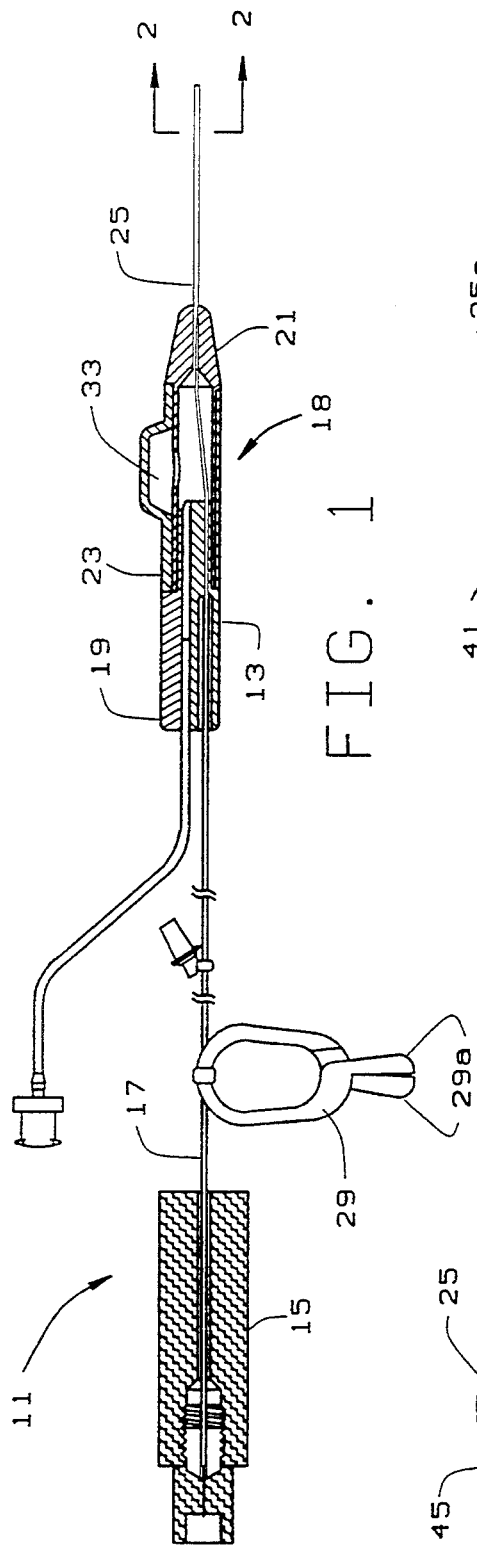
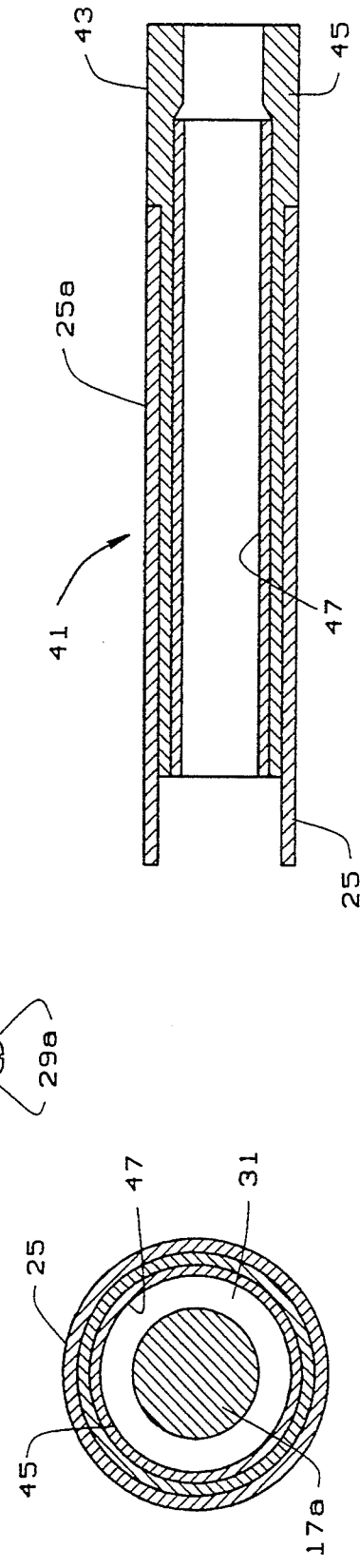
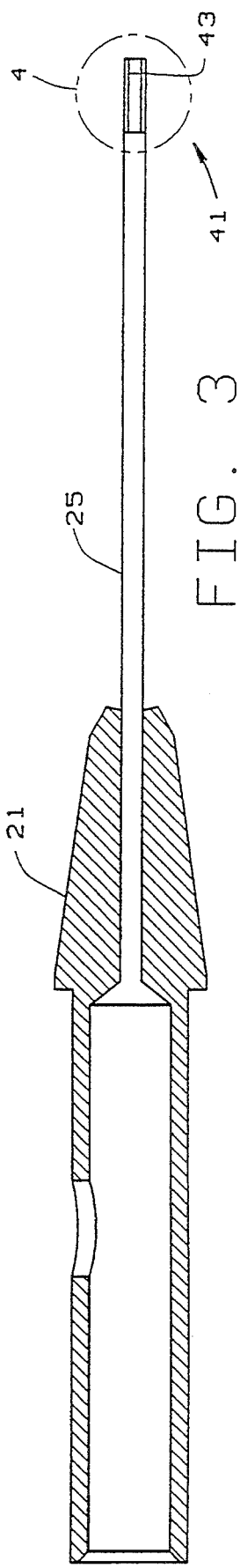

LASER DELIVERY SYSTEM WITH SOFT TIP

BACKGROUND OF THE INVENTION

The present invention relates to laser delivery systems and more particularly to such systems used in ophthalmic surgery and the like.

It is known that lasers may be used in ophthalmic surgery. Typically, the laser light is transmitted from a laser source (which is disposed at some distance from the patient) through an optical fiber cable (which can be eight feet or so in length) to the patient. The optical fiber cable terminates proximally in a laser connector (for connection to the laser source) and terminates distally in a handpiece which is manipulated by the surgeon.

Although such systems perform their desired function, they could be improved. In our copending application, Ser. No. 07/788,519, filed Nov. 6, 1991, which is incorporated herein by reference, we disclose a laser delivery system which includes a suction and reflux system integral with the handpiece so that the suction could be delivered to the exact spot where necessary, and provides the surgeon the ability to manipulate the suction with the same hand with which he manipulates the laser. This allows the surgeon to use the other hand for illumination, which is required at all times. As a result, the surgeon does not have to remove the laser probe and replace it with a suction probe when suction is desired. This replacement leads to additional time for the procedure and the possibility of additional trauma, all of which is obviated by said laser delivery system.

However, the laser delivery system can be further improved. The eye is a fragile organ and can be easily injured. The probe, which is inserted into the eye, is generally made from stainless steel. This is, of course, a rigid material, which, if inadvertently brought into contact with various structures of the eye, such as the retina, could easily injure the eye.

SUMMARY OF THE INVENTION

Among the several objects and features of the present invention may be noted the provision of an improved laser delivery system which is especially suited for ophthalmic surgery or the like.

Another object is the provision of such a system which will protect the eye from accidental contact with the laser probe to reduce injury to the eye.

A third object is the provision of such a system which is reliable, yet relatively simple to manufacture.

Other objects and features will be in part apparent and in part pointed out hereinafter.

Briefly, a laser delivery system of the present invention is especially suited for ophthalmic surgery and the like. The system includes a handpiece, a laser connector, and an optical cable. The handpiece has a handpiece body and a hollow probe of a size suitable for insertion into a human eye, which extends distally from the handpiece body. The laser connector is suitably adapted for connection to a laser source. The optical fiber (terminating proximally in the laser connector and terminating distally in the handpiece) transmits laser light from a laser source to an eye to be treated. The optical fiber extends at least partially through the handpiece probe. The probe includes a relatively hard proximal portion and a soft tip at its distal end to protect the eye from inadvertent contact with the hard portion of the probe, which could damage structures within the eye. The soft tip is a tube, preferably made of silicone, which is frictionally held in place by a bushing. The silicone tube extends beyond the distal end of the hard proximal portion of the probe. The bushing extends distally a relatively short distance from the distal end of the hard portion of the probe to hold the silicone tip straight to prevent it from bending into the laser beam.

The tube is made from constant diameter tubing having a diameter comparable to the outer diameter of the probe. It is inserted into the hard portion of the probe by inserting the bushing into the tube, inserting the tube and bushing a small distance into the hard portion of the probe, and then pushing the bushing into the hard portion of the probe, thereby extruding the tube proximally inside the hard portion of the probe. This creates a tight friction fit which holds the tube in place without the use of adhesive.

BRIEF DESCRIPTION OF THE DRAWINGS

FIG. 1 is a side view, with parts broken away for clarity, of the laser delivery system of the present invention;

FIG. 2 is an enlarged sectional view taken along line 2—2 of FIG. 1;

FIG. 3 is an enlarged sectional view of the distal end of a handpiece;

FIG. 4 is a further enlarged sectional view of the distal end of a probe of the handpiece taken along line 4—4 of FIG. 3;

Similar reference characters indicate similar parts throughout the several views of the drawings.

DESCRIPTION OF THE PREFERRED EMBODIMENT

Figure 5:
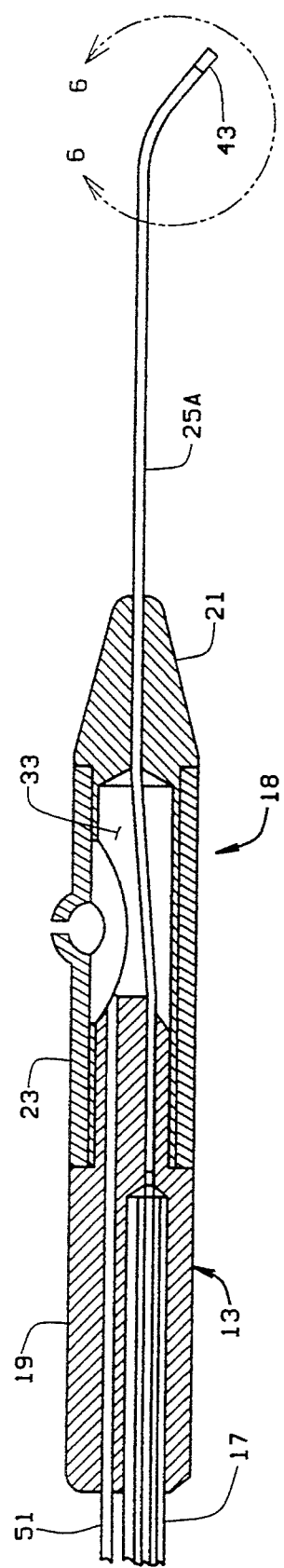
FIG. 5 is an enlarged sectional view, similar to FIG. 1, illustrating the handpiece of an alternative embodiment of the present invention.

Turning to the drawings, a laser delivery system 11 of the present invention includes a handpiece 13, a laser connector 15, and an optical fiber cable 17. Handpiece 13 has a handpiece body 18 made up of a handpiece proximal end portion 19, a handpiece distal end portion 21, and a reflux sleeve 23. A hollow probe 25 of a size suitable for insertion into a human eye extends distally from the handpiece body. Probe 25 preferably includes a metal tube or probe needle approximately one and three-quarters inches long which is suitably secured in the distal end of the handpiece body with approximately 1.38 inches of the tube exposed distally from the handpiece body. The outer diameter of the metal tube is, for example, approximately 0.0355 inch, and its inner diameter is approximately 0.030 inch. These dimensions are illustrative of those for a tip suitable for insertion in the human eye.

Laser connector 15 may be of any desired construction suitable for connection to a laser source (not shown). The construction shown is illustrative only.

As can be readily seen in FIG. 1, optical fiber cable 17 terminates proximally in laser connector 15 in such a manner that it is exposed to the laser light from the laser source. The optical cable extends for any desired length (such an eight feet or so) and terminates distally in the probe 25 of handpiece 13. Optical fiber cable 17 thereby forms an optical path for the laser light from the laser source to an eye being treated.

Also shown in FIG. 1 is a clamp 29 having jaws 29A used to removably secure cable 17 to any appropriate structure to hold the cable in place without significantly restricting movement of the handpiece by the surgeon.

Turning to FIG. 2, there is shown on a greatly enlarged scale the relationship between optical cable 17 and probe 25. The portion of optical cable 17 which is disposed in probe 25, namely an unsheathed optical fiber 17A, has an outer diameter of approximately 0.013", for example, while the inner diameter of the tip is approximately 0.020". This difference in diameter leaves a gap 31 disposed between the optical fiber and the tip. This gap runs the entire length of the tip and forms a fluid path from the distal end of probe 25 to the interior of the handpiece body.

Note that if the optical fiber were secured to probe 25 by adhesive (as has been done previously), the adhesive would tend to block off gap 31. To prevent this, the optical fiber is not secured directly to probe 25 at all. Instead it is suitably secured to proximal end portion 19 of the handpiece body. Note as well that, although the optical fiber 17 is shown centered in probe 25 in FIG. 2, the fiber can in fact be off-center in the tip without closing off gap 31.

The fluid path formed by gap 31 is in fluid communication with a cavity 33 (FIG. 1) in handpiece distal end 21. Cavity 33, in turn, is connected to a source of suction, as set forth in our above noted application. This allows fluid and other material to be withdrawn through the gap. Significantly, the distal end of this fluid path is disposed immediately adjacent the spot where the laser light exits the probe, so that removal of fluid from the operative site takes place almost exactly where needed.

The distal end 41 (see FIGS. 3 and 4) of probe 25 is provided with a tip 43 made of a soft pliable material, preferably silicone. This soft tip serves as a buffer between the structures of the eye and the metal portion of probe 25 (labelled 25A in FIG. 4), to prevent accidental injury to the eye structure caused by contact of the eye structure with the metal portion 25A of the probe. The tip 43 is made from a tube of silicone 45 (FIGS. 2 and 4) which is received within the probe metal portion 25A. Tube 45 is not fixed by adhesive in probe portion 25A. Such adhesive may block or reduce the size of the gap 31 and hence interfere with the suction. Rather, tube 45 is frictionally held in place by a bushing 47 (FIGS. 2 and 4). Tube 45 extends over bushing 47 and the bushing and tube are received within metal portion 25A of probe 25. Tip 43 extends beyond the distal end of the metal portion of probe 25 by approximately 0.040"–0.050". Tip 43 is pliable and flexible and is thus bendable. It may thus bend to a point where it would interfere with the laser beam. Bushing 47 extends beyond the metal portion of probe 25 by approximately 0.020" to add sufficient rigidity to tip 43 to prevent it from bending to a point where it would interfere with the laser beam.

Soft tubing 45 is preferably 0.037" in outer diameter. This is approximately equal to the outer diameter of probe metal portion 25A and is greater than the 0.030" inner diameter of the metal needle portion 25A of the probe (and also greater than the 0.020" inner diameter of bushing 47). To affix tube 45 within probe metal portion 25A, the bushing 47 is inserted within an elongate silicone tube having substantially constant inner and outer diameters. The tube is then scored with four 45° scores or two 90° scores spaced evenly around the tube approximately 0.025" past the end of the bushing. The tube is thus scored for a total of about 180°. Because the tube is pliable and deformable, it can be passed through the metal portion 25A of the probe until it extends out the back of the probe. In this manner, the tube is pulled into the metal portion 25A of the probe until the bushing is brought a short distance into metal portion 25A. A pull on the tube from the proximal end of the probe breaks the tube along the score lines and the excess is pulled from probe 25. The bushing is then pushed into the metal portion 25A of the probe, from the distal end of the probe, until it is inserted into the probe a desired amount.

At the time when the tube is severed along the score line, the tube, like the bushing 47, is only inserted into the metal portion 25A of the probe a short distance. By pushing the bushing into the metal portion 25A of the probe to the position shown in FIG. 4, the bushing extrudes the tube proximally along the interior of the metal portion 25A. Thus, although the tube 45 extends for between 0.15"–0.20" from end to end when completed, only approximately 0.065" of tubing is used to produce the tip. By extruding the tube 45, a very tight frictional fit is produced which holds the tube in place without the use of adhesive.

Figure 6:
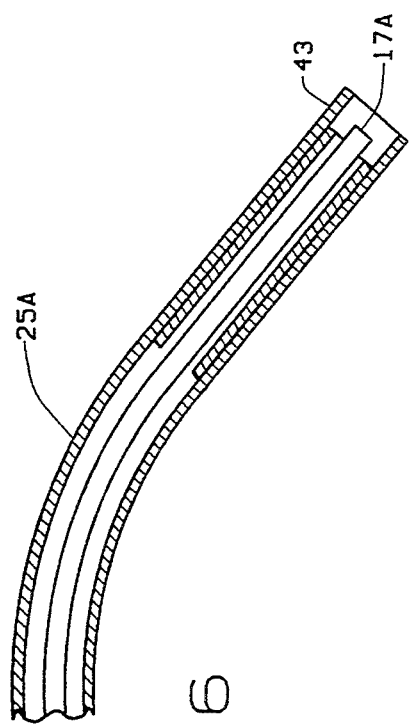
FIG. 6 is a further enlarged sectional view of the distal end of the handpiece of FIG. 5, taken along line 6—6.

Turning to FIGS. 5 and 6, a second embodiment of the present invention differs from the previous embodiment in that the distal end of the probe (labelled 25A) is curved. This enables the surgeon to access parts of the posterior segment (the interior of the eye behind the lens) that a straight probe cannot reach. Except for the curve on the end, the curved and straight probes are identical. The distal end of the probe is curved to form an angle (such as the 40 degree angle shown in FIG. 5) with respect to the longitudinal axis of the probe and handpiece. The probe is preferably bent starting proximal to the soft tip 43 itself (as best seen in FIG. 6). Alternatively, the bend could start at the tip itself, but that would complicate the bending process, and would not significantly improve the useability of the device by the surgeon. Although the particular radius of the curved portion of the tip can vary, depending upon the desired application, a radius of approximately ¼" was used in the device of FIGS. 5 and 6.

Figure 7:
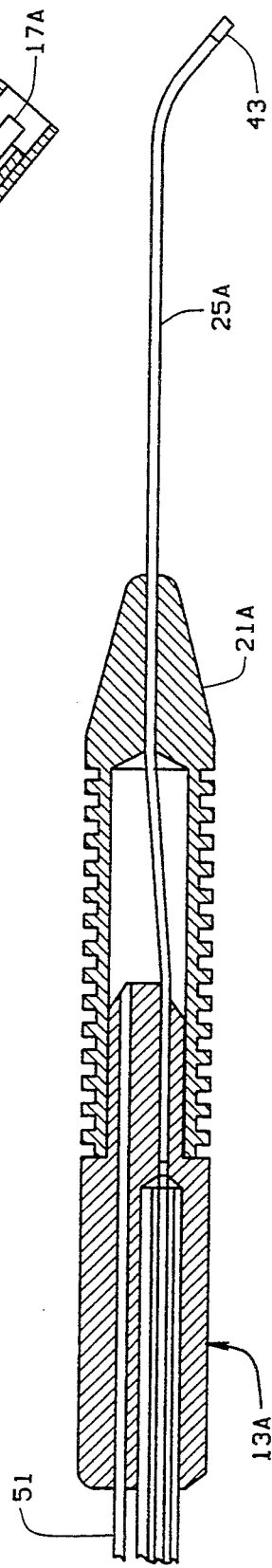
FIG. 7 is a sectional view, similar to FIG. 5, illustrating another embodiment of the present invention.

Turning to FIG. 7, yet another embodiment of the handpiece is shown. This handpiece, labelled 13A, differs from that of FIG. 5 mainly in that the distal portion 21A of the handpiece does not include the reflux capability of the handpieces of FIGS. 1, and 5. It has no provision for passive aspiration.

Typically, port 51 of the handpiece is connected to a syringe or a typical surgery machine that can supply suction for active aspiration. Handpiece 13A can function well without reflux because of the soft tip 43 and the type of suction used. For example, if the surgeon uses passive aspiration with the device of FIG. 1, it is possible for a membrane or part of the retina to be caught on the probe tip. Because fragile tissue caught in the hard tip of FIG. 1 will probably tear if the surgeon tries to pull the probe away, the reflux capability of the probe of FIG. 1 allows the surgeon to reflux the captured material back into the eye without damage to these fragile tissues.

When the surgeon uses passive aspiration with a probe having soft tip 43, it is doubtful whether any tissues caught in the tip would tear when the surgeon would try to pull the tip away. In that case the reflux capability of the probes shown in FIGS. 1 and 5 is not necessary. If the surgeon uses active aspiration with a probe having soft tip 43, the soft tip again reduces the possibility of tearing as the probe is pulled away. In any event, however, with active aspiration the aspiration or suction source may be used to provide reflux without the separate reflux structure shown in FIGS. 1 and 5. For these applications, the handpiece of FIG. 7 without the separate reflux structure works well, is simpler to make, and is relatively less expensive than the embodiments of FIGS. 1 and 5.

In view of the above it will be seen that the various objects and features of the above described invention are achieved and other advantageous results obtained. The description and drawings of the present invention contained herein are illustrative only and are not to be interpreted in a limiting sense.

We claim:

1. A laser delivery system for ophthalmic surgery and the like comprising:
    a handpiece having a handpiece body and a hollow probe of a size suitable for insertion into a human eye, said hollow probe extending distally from the handpiece body and having a proximal portion and a distal end, said hollow probe including a metal tube forming the proximal portion of the probe, said metal tube being fixedly secured against longitudinal and rotational movement with respect to the handpiece body;
    a laser connector for connection to a laser source;
    an optical fiber terminating at one end in the laser connector and terminating at another end in the handpiece for transmitting laser light from said laser source to an eye to be treated; and
    a relatively straight soft tip forming the distal end of said probe, said soft tip being fixedly secured against longitudinal and rotational movement with respect to said metal tube;
    wherein said soft tip comprises a tube frictionally held in said probe and which is made of a soft pliable material, said soft pliable material being received at least partly in said metal tube and extending distally beyond said metal tube;
    said soft pliable tube being received over a bushing, said bushing frictionally holding said soft pliable tube in said metal tube with the soft pliable tube captured between the bushing and the metal tube.

2. The laser delivery system of claim 1 wherein said bushing is disposed partially within said metal tube and extends distally out of said metal tube.

3. The laser delivery system of claim 2 wherein said bushing includes a distal end, said soft pliable tube extending beyond the distal end of said bushing.

4. A handpiece for an ophthalmic laser delivery system including a handpiece body and a probe of a size suitable for insertion in a human eye extending from an end of said handpiece, said probe being fixedly secured against longitudinal and rotational movement with respect to the handpiece body, said probe having a relative straight soft tip and a proximal portion, said soft tip being fixedly secured against longitudinal and rotational movement with respect to the proximal portion of the probe;
    wherein the proximal portion of said probe is composed of a relatively hard material and said soft tip comprises a tube made of a soft pliable material which is received at least partly in said hard proximal portion of said probe and extends distally beyond said hard proximal portion of said probe:
    said soft pliable tube being frictionally held in said hard proximal portion of said probe; said soft pliable tube being received over a bushing, said bushing frictionally holding said soft pliable tube fixed in place with respect to said hard proximal portion of the probe with the soft pliable tube captured between the bushing and the metal tube.

5. The handpiece of claim 4 wherein said bushing is disposed partially within said hard proximal portion of said probe and extends distally out of said hard proximal portion.

6. The handpiece of claim 5 wherein the bushing includes a distal end, said soft pliable tube extending beyond the distal end of said bushing.

* * * * *